United States Patent [19]

Higashi et al.

[11] Patent Number: 4,981,693

[45] Date of Patent: Jan. 1, 1991

[54] PHARMACEUTICAL COMPOSITION FOR PERIODONTAL DISEASES

[75] Inventors: Kiyotsugu Higashi, Nara; Shigeru Kametaka, Osaka; Katsuhiko Morisaki, Nara; Shin'ichi Hayashi, Osaka, all of Japan

[73] Assignee: Rohto Pharmaceutical Co., Ltd., Osaka, Japan

[21] Appl. No.: 414,598

[22] Filed: Sep. 29, 1989

Related U.S. Application Data

[63] Continuation of Ser. No. 29,657, Mar. 24, 1987, abandoned.

[30] Foreign Application Priority Data

May 25, 1986 [JP] Japan .................... 61-67811

[51] Int. Cl.⁵ .................... A61K 9/06; A61K 9/70; A61K 31/78
[52] U.S. Cl. .................... 424/435; 424/443; 424/78; 424/81; 514/781; 514/900; 514/902; 514/953; 514/969
[58] Field of Search .................... 424/78, 81, 435, 443; 514/781, 900, 902, 953, 969

[56] References Cited

U.S. PATENT DOCUMENTS

| | | | |
|---|---|---|---|
| 4,426,373 | 1/1984 | Morton et al. | 424/49 |
| 4,482,535 | 11/1984 | Sugar et al. | 424/49 |
| 4,537,765 | 8/1985 | Graffar et al. | 424/49 |
| 4,550,018 | 10/1985 | Ambike et al. | 424/49 |
| 4,569,837 | 2/1986 | Suzuki et al. | 424/435 |
| 4,661,341 | 4/1987 | Benedict et al. | 424/49 |
| 4,663,152 | 5/1987 | Barth et al. | 424/49 |
| 4,681,544 | 7/1987 | Anthony | 433/215 |
| 4,701,320 | 10/1987 | Hasegawa et al. | 514/900 |
| 4,702,905 | 10/1987 | Mitchell et al. | 424/49 |
| 4,713,243 | 12/1987 | Schiraldi et al. | 424/435 |
| 4,740,365 | 4/1988 | Yukimatsu et al. | 424/435 |
| 4,764,377 | 8/1988 | Goodson | 424/435 |

FOREIGN PATENT DOCUMENTS

| | | | |
|---|---|---|---|
| 184389 | 6/1986 | European Pat. Off. | 514/900 |
| 2404257 | 8/1975 | Fed. Rep. of Germany | 424/486 |
| 2109237 | 6/1983 | United Kingdom | 424/486 |

*Primary Examiner*—Shep K. Rose
*Attorney, Agent, or Firm*—Robbins & Laramie

[57] ABSTRACT

A pharmaceutical composition for treating periodontal diseases which comprises one or more of therapeutically active ingredients admixed with a polymer capable of dissolving in an aqueous medium of pH 4.0 or higher.

2 Claims, 1 Drawing Sheet

PHARMACEUTICAL COMPOSITION FOR PERIODONTAL DISEASES

RELATED APPLICATION

This is a continuation of U.S. patent application Ser. No. 029,657, filed Mar. 24, 1987, now abandoned.

This invention relates to a pharmaceutical composition which is applied to a periodontal pocket or paradentium for the purpose of treating periodontal diseases. More particularly, it relates to a pharmaceutical composition which allows a therapeutically active ingredient contained in the composition to be released in response to the pH change of the effusion of the lesional region, which occurs in the course of development or progress of the periodontal diseases.

The "periodontal diseases" is a general term of various inflammatory diseases of paradentium. The diseases include a series of diseases exhibiting various syndromes which vary from each other according to the stage or situation of the diseases or the age of the patient, and have not been definitely subclassified. Since, however, the term "periodontal diseases" is given to any inflammatory disease which initially occurs at a marginal gingiva area and finally reaches an alveolar bone, the diseases can be roughly divided, on the basis of the degree of the inflammation, into "gingivitis" in which the inflammation is limited to the gingiva tissue, and "paradentitis" in which the inflammation is chronic and found even in an alveolar bone. However, peculiar diseases such as "juvenilie paradentitis" and "acute necrotizing ulcerative gingivitis" are also included in the periodontal diseases.

The paradentitis, which was once called "alveolar pyorrhea", is characterized by remarkable symptoms such as inflammation of gingiva, formation of periodontal pockets, bleeding and pus discharge from said periodontal pockets, and it brings about resorption of alveolar bone, loose tooth, and shedding of tooth.

The consensus of most investigators is that the periodontal diseases is caused by bacteria present in dental plaques formed in periodontal pockets. Efforts have been concentrated on the discovery of pathogenic bacteria responsible for said diseases. At the present time, an attributable major pathogen is recognized to be a certain nigral pigment-producing bacteria, such as genus Bacteroides. However, other genus of bacteria including Actinobacillus, Capnocytophaga, Fusobacterium and Spirochetes may be included in the causative pathogens. In any case, it is an established theory that the periodontal diseases should not be attributed to all bacteria present in the dental plaque.

With progression of periodontal diseases, the pH of the effusion of the legional region goes up to 7.6, while it remains 6.5 in normal state.

The periodontal diseases has previously been treated by several ways, such as exhaustive scaling of plaques in periodontal pockets, root plainning, gingivectomy to eliminate the periodontal pocket, or surgical curettage to excise inflammatory tissues. These treatments have been effective to some extent but not satisfactory.

On the other hand, pharmacotherapy has also been conducted using a drug selected from germicides, anti-inflammatory agents, plaque solubilizing agents, hemostyptics, and the like. These drugs are used in the form of the formulation suited for internal use or massotherapy (e.g., dentifrices, ointments, and the like). However, they are not satisfactory for the purpose of treatment of periodontal diseases because the internal use hardly permits the selective migration of the drug to the lesional region, and the massotherapy is not successful in solubilizing the plaques which are present beneath the gingival margin.

Recently, several strips which comprise polymers and active ingredients for treatment of periodontal diseases have been developed. These strips are said useful for the treatment of plaques and inflammation beneath the gingival margin. The strips can be applied directly to the lesional region to be treated, and therefore, the active ingredient can be concentrated to the desired site selectively. This modified therapeutic method has been proved to be more effective than any conventional pharmacotherapy. For instance, J. M. Goodson et al. disclose the implantation of "hollow fiber", which contains germicides, into gingival region (J. Clinical Periodontology, 1979: 6: 83-92). M. Addy et al. have reported the insertion of strips, which were prepared from a mixture of an insoluble polymer such as polyethylmethacrylate and germicides, into periodontal pockets (J. Periodontal, 693, Nov. 1982). In addition, insertion of the strips, prepared from a mixture of a soluble polymer and a drug, into the lesional region, such as periodontal pockets, is also reported (Japan Patent Publication No. 59-222406).

However, the formulations mentioned above constantly release a predetermined amount of the active ingredient irrespective of the deterioration or restoration of the disease. Accordingly, a great care is required for administration of these formulations in order to provide suitable amount of the active ingredient to the locus of the disease. In order to overcome the above inconvenience, it has long been desired to establish a formulation which will release a predetermined amount of an active ingredient depending on the state of the disease, i.e., only when such release is necessary and desirous.

The inventors of the present invention have paid attention to the fact that the extended inflammation in periodontal diseases is always accompanied by an elevation of the pH of the effusion present in the associated gingival crevice, and that such elevated pH is lowered when the inflammation becomes declined and subsided. On the basis of the above fact, the inventors have started the study seeking for the formulation, from which an active ingredient is released with different releasing rates depending on the pH change of the effusion in a periodontal pocket to which the formulation is applied. As the results of the study, it has been found that a composition comprising a mixture of an active ingredient and a polymer capable of dissolving in an aqueous medium at a pH of 4.0 or higher, meets the requirements as mentioned above.

The present invention is based on the above finding and provides a pharmaceutical composition for treating periodontal diseases which comprises one or more of therapeutically active ingredients admixed with a polymer capable of dissolving in an aqueous medium of pH 4.0 or higher.

Figure 1:
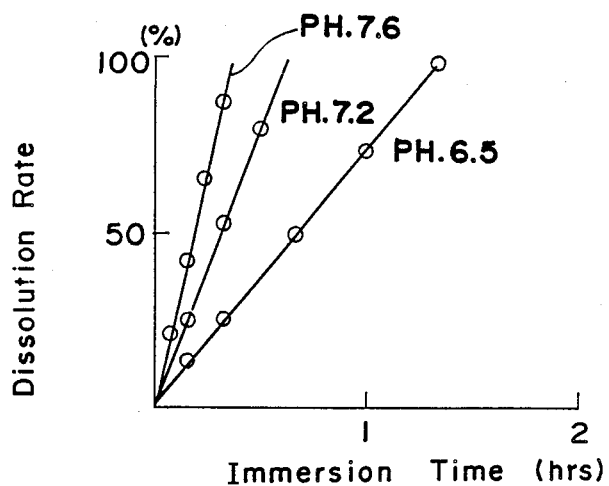
FIG. 1 shows the dissolution profile of a therapeutically active ingredient contained in the pharmaceutical composition of the invention which comprises a polymer capable of dissolving in an aqueous medium of pH 6.0 or higher.

The polymer which is capable of dissolving in an aqueous medium having a pH above 4.0 (such polymer will be hereinafter referred to as "a polymer having a limited solubility" for simplicity) includes copolymers consisting of acrylic acid, methacrylic acid and/or esters thereof, such as methyl acrylate / methacrylic acid copolymer, methyl acrylate / methacrylic acid / octyl acrylate copolymer, ethyl acrylate / methacrylic acid copolymer, methyl acrylate / methacrylic acid / methyl methacrylate copolymer, and methyl methacrylate / methacrylic acid copolymer, hemiesters of organic bivalent acid with polysaccharide acetates such as cellulose acetate phthalate, cellulose acetate succinate, cellulose acetate maleate, starch acetate phthalate, and amylose acetate phthalate, hemiesters of organic bivalent acid with alkylated polysaccharides such as methyl cellulose phthalate, hemiesters of organic bivalent acid with hydroxyalkylated polysaccharide such as hydroxypropylmethyl cellulose phthalate, and hydroxyethyl ethyl cellulose phthalate, hydroxypropylmethyl cellulose acetate succinate, alkyl ethers of carboxyalkylated polysaccharide such as carboxymethylethyl cellulose, hemiesters of organic bivalent acid with polyvinyl alcohol and its derivatives such as polyvinyl alcohol phthalate, polyvinyl acetate phthalate, polyvinyl acetal phthalate, and polyvinyl butylate phthalate.

The polymers listed above can be prepared so as to have a desired solubility by, for example, adjusting the degree of polymerization or loads of monomers. Accordingly, a particular pH, at which the composition of the invention is desirous to start dissolution, can be determined as desired by selecting a single polymer from the above-listed polymers. However, the desirous pH may be also determined by blending two or more of these polymers.

In addition, for the purpose of the present invention, a mixture consisting of one or more polymers selected from the polymers listed above and one or more polymers which are freely soluble in an aqueous medium can be employed.

Accordingly, the term "a polymer capable of dissolving in an aqueous medium of pH 4.0 or higher" or "a polymer having a limited solubility" herein used means not only a single polymer capable of dissolving in an aqueous medium of pH 4.0 or higher, but also a mixture of two or more kinds of said polymers and a mixture of said polymer(s) and one or more water soluble polymers, as far as any contradiction will not arise.

Therapeutically active ingredient or ingredients used for the preparation of the composition of the invention are selected from those effective for prevention or treatment of periodontal diseases, for example, germicides, such as chlorhexidine, Ag protein, glyceryl iodide, phenol, benzalkonium chloride, cetylpyridinium chloride, and the like; antimicrobial agents, such as ampicillin, tetracycline, benzylpenicillin, clindamycin, cefalexin, erythromycin, chloramphenicol, fragiomycin sulfate, and the like; anti-inflammatory agents, such as ibuprofen, indomethacin, ketoprofen, mefenamic acid, antipyrine, pranoprofen, ibufenac, tiaramide hydrochloride, prednisolone, dexamethasone, triamcinolone acetonide, prostaglandin, and the like; plaque solubilizing agents, such as dextranase, protease, amylase and the like; collagenase inhibitors obtained from the extraction of crude drugs, such as gambir-catechu known in the name of "asenyaku"; local anesthetics, such as tetracaine hydrochloride, ethyl aminobenzoate, and the like; antihistaminic agents, such as chlorphenilamine maleate, diphenhydramine, and the like; hemostatic agents such as tranexamic acid, and the like.

The pharmaceutical composition of the invention may be prepared by mixing one or more of active ingredients with a polymer having a limited solubility and, if necessary, a suitable water soluble polymer, and forming the resultant mixture into a homogeneous solid material in the form of film, sheet or bar.

The composition may also be prepared in the form of film laminates composing of one or more layer(s) of a polymer having a limited solubility and one or more layer(s) of water soluble polymers, each layer containing different amount of, or different kind of, active ingredient. In addition, the composition of the invention may comprise solid particles consisting of an active ingredient and a polymer having a limited solubility, said particles being dispersed in a carrier in the form of gel or ointment. The active ingredient may also be contained in the carrier.

The solid composition of the invention in the form of film, sheet or bar can be prepared in different sizes. However, the convenient size of the film or sheet may be 0.1 - 0.5 mm in thickness, 0.5 - 3.0 mm in width, and 10 - 50 mm in length. The size of the bar may generally range from 0.5 to 1.5 mm in diameter and from 10 to 50 mm in length. Furthermore, the composition of the invention may be cut in a suitable size by the user depending on several factors, such as severity of the disease, and the width and depth of the locus to be applied.

The composition of the invention can be applied to the periodontal pocket or paradentium by insertion, injection, or rubbing according to the type of formulation.

The pharmaceutical composition of the invention may include one or more of pharmaceutically acceptable plasticizers, preservatives, pH regulating agents, base materials for preparing film or ointment, lubricants and/or stabilizers.

Following examples illustrate the preparation of the composition of the present invention. In examples, part or parts are represented by weight basis.

EXAMPLE 1

Methacrylic acid / methyl methacrylate copolymer (1:1 molar ratio) (30 parts) and methacrylic acid / methyl methacrylate copolymer (1:2 molar ratio) (50 parts) are dissolved in ethanol (1000 parts). In the solution are dissolved or suspended triacetin (20 parts) and tetracycline (10 parts), and the mixture is uniformly casted into a sheet, which is then dried at 40° C. A film composition of 300µ in thickness is thus obtained.

EXAMPLE 2

The film composition obtained in Example 1 is pulverized into particles having an average size of 70µ. The particles (40 parts), plastibase (30 parts) and hydroxypropyl cellulose (30 parts) are uniformly admixed to obtain an ointment composition.

EXAMPLE 3

Carboxymethylethyl cellulose (70 parts), triacetin (30 parts) and tetracycline (5 parts) are uniformly admixed. After addition of a small amount of ethanol, the mixture is extruded and dried to yield a bar composition having a diameter of 1.0 mm.

EXAMPLE 4

Hydroxypropylmethylcellulose acetate succinate (succinoyl 5.5%, acetyl 10.9%, methoxyl 23.9%, hydroxypropoxyl 7.3%) (80 parts) is dissolved in ethanol (1000 parts). To the solution are added triacetin (20 parts) and predonisolone (3 parts). The mixture is casted on a Teflon tray and dried to obtain a film having a thickness of 150.

On the other hand, pullulan (80 parts), polyethylene glycol 400 (20 parts), and chlorhexidine hydrochloride (2 parts) are dissolved or suspended in water (1000 parts). After adjusted to pH 5.0 with hydrochloric acid, the mixture is casted on the film obtained above and dried to obtain a two-layer laminated film having a thickness of 300μ.

EXPERIMENT 1

As will be detailed below, a pharmaceutical composition in the form of a film was prepared using an active ingredient and methacrylic acid / methyl methacrylate copolymer which dissolves in an aqueous medium having a pH above 6.0. Similar composition was prepared by the use of methacrylic acid / methyl methacrylate copolymer which dissolves in an aqueous medium having a pH above 7.0. The release rates of the active ingredient of respective compositions were measured by dipping them in several aqueous media having a pH ranging from 6.5 to 7.6. A consisting of hydroxypropyl cellulose and the same active ingredient was used as a control.

PREPARATION OF FILMS (A) Methacrylic acid / methyl methacrylate copolymer (1:1 molar ratio) (80 parts) was dissolved in ethanol (1000 parts). In the solution were dissolved triacetin (20 parts) and tetracycline hydrochloride (5 parts), and the resultant mixture was casted on a Teflon tray and air-dried at 40° C. to obtain a film of 200μ in thickness, which dissolves at pH 6.0 or higher.

(B) The above procedure was repeated using methacrylic acid / methyl methacrylate copolymer (1:2 molar ratio) to obtain a film which dissolves at pH 7.0 or higher.

(C) Hydroxypropyl cellulose (2% aqueous solution, viscosity: 1000-4000 cps at 20° C.) (80 parts) was dissolved in ethanol (1000 parts). Triacetin (20 parts) and tetracycline hydrochloride (5 parts) were blended with the resultant solution. The mixture was treated in the same manner as above to obtain a film having a thickness of 200μ. This film was employed as a control.

EVALUATION OF DISSOLUTION RATE

The dissolution rates of the active ingredient released from the films obtained above were measured using a phosphate buffer (500 ml), pH 7.2, at 37° C in accordance with the Rotating Basket Method (100 rpm) of Japanese Pharmacopocia (X).

RESULTS

Figure 2:
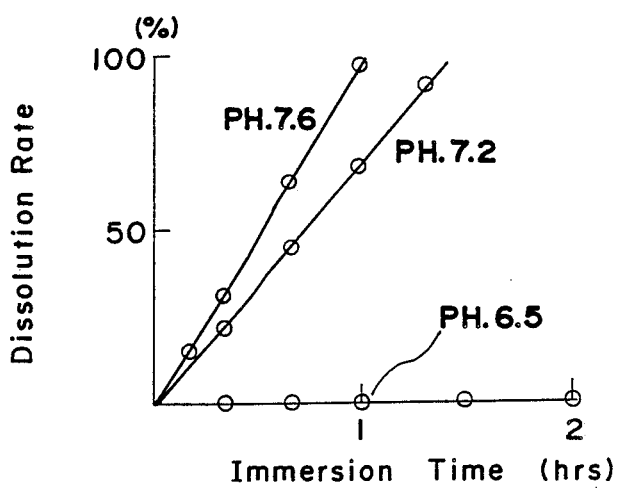
FIG. 2 shows the dissolution profile of a therapeutically active ingredient contained in the pharmaceutical composition of the invention which comprises a polymer capable of dissolving in an aqueous medium of pH 7.0 or higher.
Figure 3:
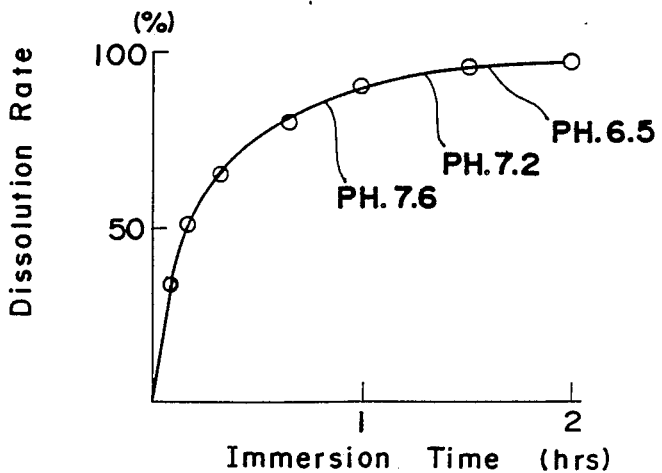
FIG. 3 shows the dissolution profile of a therapeutically active ingredient contained in a reference composition which comprises a freely-soluble polymer.

The dissolution profile of each of the films obtained in (A), (B) and (C) above is shown in FIG. 1, FIG. 2 and FIG. 3 of the accompanying drawing. FIGS. 1 and 2 show that the dissolution rates of respective films of the invention changed depending on the pH of the buffer in which the films were immersed, while no change was observed on the dissolution rate of the control.

What we claim is:

1. A controlled-release pharmaceutical composition to be inserted or placed into a periodontal pocket for treating a periodontal disease comprising a therapeutically effective amount of an active agent effective for the treatment of the periodontal disease, said active agent being admixed with a polymer capable of dissolving in an aqueous medium of pH 4.0 or higher and incapable of dissolving in an aqueous medium of below pH 4.0, said composition being in the form of film, sheet, strip, gel or ointment, and said polymer being selected from the group of methylacrylate/methacrylic acid copolymer, methylacrylate/methacrylic acid/octylacrylate copolymer, ethylacrylate/methacrylic acid copolymer, methylacrylate/methacrylic acid/methylmethacrylate copolymer, methylmethacrylate/methacrylic acid copolymer, cellulose acetate phthalate, cellulose acetate succinate, cellulose acetate maleate, starch acetate phthalate, amylose acetate phthalate, methyl cellulose phthalate, hydroxypropyl methylcellulose phthalate, hydroxyethylenthylcellulose phthalate, hydroxypropyl methylcellulose acetate succinate, carboxymethylethylcellulose, polyvinylalcohol phthalate, polyvinylacetate phthalate, polyvinylacetal phthalate, and polyvinylbutylate phthalate, 2. In the art of applying an active ingredient useful for the treatment of periodontal disease dispersed in a polymeric carrier directly into a periodontal pocket to thereby be released from the carrier at pHs of 4.0 or higher, said pHs always accompanying periodontal disease, the improvement consisting of the step of placing in the periodontal pocket a gel, sheet, ointment, strip or film consisting of a therapeutically effective amount of the active ingredient admixed with a polymer capable of dissolving in an aqueous medium of pH 4.0 or higher and incapable of dissolving in an aqueous medium of pH below 4.0, said polymer selected from the group consisting of methylacrylate/methacrylic acid copolymer, methylacrylate/methacrylic acid/octylacrylate copolymer, ethylacrylate/methacrylic acid copolymer, methylacrylate/methacrylic acid/methylmethacrylate copolymer, methylmethacrylate/methacrylic acid copolymer, cellulose acetate phthalate, cellulose acetate succinate, cellulose acetate maleate, starch acetate phthalate, amylose acetate phthalate, methyl cellulosephthalate, hydroxypropyl methylcellulose phthalate, hydroxyethyl ethylcellulose phthalate, hydroxypropyl methylcellulose acetate succinate, carboxymethylethylcellulose, polyvinylalcohol phthalate, polyvinylacetate phthalate, polyvinylacetal phthalate, and polyvinylbutylate phthalate.

* * * * *